US008859211B2

(12) United States Patent
Chaffey et al.

(10) Patent No.: US 8,859,211 B2
(45) Date of Patent: Oct. 14, 2014

(54) IMMUNODISPLACEMENT ELECTROPHORESIS

(75) Inventors: Ben Chaffey, Newcastle-upon-tyne (GB); Joanne Baxter, Blyth (GB); Kevin Waltham, Newcastle-upon-Tyne (GB); Beverly Askew, Newcastle-upon-Tyne (GB)

(73) Assignee: Helena Laboratories (UK) Ltd., Gateshead (GB)

( * ) Notice: Subject to any disclaimer, the term of this patent is extended or adjusted under 35 U.S.C. 154(b) by 518 days.

(21) Appl. No.: 12/610,099

(22) Filed: Oct. 30, 2009

(65) Prior Publication Data

US 2010/0113752 A1 May 6, 2010

(30) Foreign Application Priority Data

Nov. 3, 2008 (EP) .................................... 08168195

(51) Int. Cl.

*G01N 33/53* (2006.01)
*G01N 27/26* (2006.01)
*C07K 16/00* (2006.01)
*B01D 57/02* (2006.01)
*G01N 33/561* (2006.01)

(52) U.S. Cl.

CPC .................................... *G01N 33/561* (2013.01)
USPC ...... 435/7.1; 530/387.1; 530/391.1; 204/450; 204/451; 204/600; 204/601

(58) Field of Classification Search

None
See application file for complete search history.

(56) References Cited

U.S. PATENT DOCUMENTS

| | | | | |
|---|---|---|---|---|
| 5,567,282 | A * | 10/1996 | Wang et al. | 204/450 |
| 2005/0164302 | A1 | 7/2005 | Robert et al. | |
| 2005/0170362 | A1 * | 8/2005 | Wada et al. | 435/6 |

FOREIGN PATENT DOCUMENTS

| | | |
|---|---|---|
| WO | WO 95/20160 | 7/1995 |
| WO | WO00/26256 | 5/2000 |

OTHER PUBLICATIONS

A printout from http://www.synonym.com/definition/conjugated, retrieved May 22, 2012.*
EP Search Report EP 08168195.9 completed Jan. 19, 2009.
Li and Kricka (2006) Clinical Chemistry 52(1):37-45, “Clinical Analysis by Microchip Capillary Electrophoresis”.
Narula et al.(Jan. 1, 1995) Journal of Nuclear Cardiology, 2(1):26-34, “In vivo targeting of acute myocardial infarction with negative-charge, polymer-modified antimyosin antibody: Use of different cross-linkers”.
Shimuara et al. (1987) Electrophoresis 8:135-139, “Affinophoresis of anti-hapten antibody in rabbit serum with an anionic affinophore bearing the hapten”.
Shimuara et al. Electrophoresis 19:397-402, “Capillary affinophoresis of pea lectin with polyliganded affinophores: A model study of divalent-polyvalent interactions”, 1998.

* cited by examiner

*Primary Examiner* — Galina Yakovleva
(74) *Attorney, Agent, or Firm* — Swanson & Bratschun, L.L.C.

(57) ABSTRACT

The disclosure teaches a method for the analysis of a sample by electrophoresis, making use of a binding partner for a target compound or group of target compounds which may be present in the sample. The disclosure further teaches a kit for use in an electrophoretic analysis, to a modified antibody or fragment thereof, and to specific uses of the kit or modified antibody or fragment thereof.

19 Claims, 2 Drawing Sheets

IMMUNODISPLACEMENT ELECTROPHORESIS

RELATED APPLICATIONS

This application claims priority from European Patent Application Serial No. 08168195.9, filed Nov. 3, 2008, entitled "Immunodisplacement Electrophoresis," which is hereby incorporated by reference in its entirety.

TECHNICAL FIELD

Electrophoresis has been a well-established method for analyzing various samples, including samples comprising biological compounds such as proteins, for many decades. The disclosure teaches a method for the analysis of a sample by electrophoresis, making use of a binding partner for a target compound or group of target compounds which may be present in the sample. The disclosure further teaches a kit for use in an electrophoretic analysis, to a modified antibody or fragment thereof, and to specific uses of the kit or modified antibody or fragment thereof.

BACKGROUND

Over the years well-established methods have been developed. For instance, the separation of serum proteins in a series of characteristic bands, commonly referred to as gamma, beta, alpha-1 and 2 and albumin by electrophoresis is well know to those skilled in the art and is well described in a wide range of reference materials, such as the handbook 'Protein Electrophoresis in Clinical Diagnosis' by David F. Keren, 2003, Arnold Publications.

Commonly known methods include the use of techniques wherein a specific compound is subjected to a complexation with a specific binding partner, such as an antibody against that compound. Such techniques may be used to remove the compound from the sample prior to electrophoretic separation (typically referred to as immunosubtraction when an antibody is used as a binding partner) or to modify the effective electrophoretic mobility of that compound during electrophoresis (referred to as immunodisplacement when an antibody is used as a binding partner).

The target compound that forms a complex with the binding partner may be a compound that is to be identified, e.g. a monoclonal immunoglobulin which may be an indicator for a monoclonal gammopathy. In cases where the binding partner is an antibody this method may be referred to as immunotyping.

Alternatively, the target compound may be an interfering factor, i.e. potentially disturbing the analysis of a sample for another compound of which the presence is to be determined, by, for example, co-migrating with the analyte of interest or in other ways masking it's presence, e.g. a gamma-globulin which may migrate very close to carbohydrate-deficient isoforms of transferrin and hence impede their use as a diagnostic marker for excessive alcohol consumption Capillary electrophoresis is a specific form of electrophoresis, wherein a capillary is used to perform the electrophoresis. Capillary electrophoresis offers advantages such as short analysis times and a high resolution. A method for the capillary electrophoretic analysis of a sample comprising a compound of which the presence is to be determined (i.e. analyte), wherein use is made of an antibody as a binding partner for the analyte is described in WO 95/20160. The method involves:

(a) separating a first portion of the sample into constituent analyte parts by capillary electrophoresis, and detecting said parts;

(b) admixing a second portion of said sample with at least one specific binding partner to a predetermined candidate analyte, said specific binding partner having an electrophoretic mobility different from that of said candidate analyte, hence conferring to the resulting complexes formed an electropheric mobility different to the unbound analyte;

(c) separating said second portion into constituent parts by capillary electrophoresis, and detecting said parts; and, (d) comparing the separated constituent parts of step (c) with the separated constituent parts of step (a).

As a specific binding partner preferably an antibody is used that has been chemically modified with an anhydride, such as succinic anhydride, to provide the antibody with additional carboxylic acid functions, negative at alkaline pH. Under the analytical conditions described in the example (pH 10) the overall negative charge of the modified antibody is therefore increased, compared to the unmodified antibody. However, as shown in FIG. 1 of WO95/20160, the modified antibody still migrates closely to human immunoglobin (IgG) and in particular the complex of the modified antibody with IgG is not fully separated from uncomplexed IgG. It is apparent that in a real biological sample which is to be analysed for the presence of one or more serum proteins (e.g. blood serum, urine, cerebrospinal fluid), the electrophoretic migration of the modified antibody and in particular of the complex of antibody and immunoglobin in the sample would be such that they may co-migrate with serum proteins, for instance, another immunoglobin, a transferrin, albumin or bis-albumin, for which the sample is to be analysed.

US 2005/0164302 A1 proposes an alternative method of separating the constituents of a biological sample and carrying out immunodisplacement to allow typing of monoclonal proteins which may be present in the analysed biological sample. It is mentioned that the method allows displacement outside the zone corresponding to the migration profile for the proteins of the sample, in particular outside the globulin migration zone. This is said to be accomplished by modifying the binding partner (an antibody) in a specific way. The specific modifications shown are a modification of the antibodies with tricarboxylic anhydride and modification with mellitic acid. From the Examples it is apparent that the modified antibody has an effect in that immunodisplacement takes place, but it is also apparent that modified antibody or complex of modified antibody and immunoglobulin of the sample is not fully separated from other proteins in the sample. Notably, several electropherograms, e.g. FIGS. 2e, 4b, 5a, 9a and 9b of US 2005/0164302 A1, suggest an overlap with albumin and possibly other proteins migrating between albumin and the immunoglobulins of the sample. Further, in a test performed by the present inventors the migration time of an unmodified antibody (IgG) and an antibody (IgG) modified with benzene tricarboxylic acid anhydride in a buffer at pH 10 (comprising 3-cyclohexylamino-1-propanesulphonic acid (CAPS) and N-Tris(hydroxymethyl)methyl-3-aminopropanesulphonic acid (TAPS)), it was found that the modified antibody had a migration time (peak top time) that was similar to the migration time of albumin, indicating that the modified antibody would not be baseline-separated from albumin in a blood serum sample. Further, this is an indication that a complex of the modified antibody and an immunoglobin in a serum sample may have a migration time in between the migration time of immunoglobins and the migration time of albumin. Thus, the complex would likely at least partially co-migrate with other proteins, e.g. the alpha-band serum proteins, in an electrophoretic analysis using such a buffer. Thus, it remains a challenge to avoid undesired co-migration of the complex, especially in the separation of a complicated sample, such as a blood serum or another biological sample.

The present disclosure is directed toward overcoming one or more of the problems discussed above.

SUMMARY OF THE EMBODIMENTS

It is an object of the present disclosure is to provide a novel method for analyzing a sample, in particular a sample of a body fluid which may comprise one or more serum proteins, for the presence of one or more compound of interest, such as one or more serum proteins, making use of a binding partner, such as an antibody or fragment thereof, which is capable of binding to a specific target compound, which may be a compound of which the presence is to be determined (an analyte) or a compound that may interfere with the analysis of the sample.

It is an objective of the disclosure to provide a method that allows baseline separation of the binding partner, and preferably of a complex of the binding partner and the target compound, from any component of the sample, or at least of any protein of which the presence is to be determined.

One or more other objectives that may be met in accordance with the invention will become apparent from the description and/or claims.

The inventors have found that it is possible to use a binding partner that has been modified in a specific way in an electrophoretic analysis method.

Accordingly, the present disclosure teaches a method for the analysis of a sample which may comprise a target compound or group of target compounds, the method comprising mixing at least a portion of the sample with a binding partner for the target compound or group of target compounds, the binding partner being a macromolecule comprising (i) a segment capable of specifically binding to the target compound and (ii) a polyanionic polymer segment; and separating the sample including the binding partner by electrophoresis in a separation medium in which the binding partner has a negative charge.

In one embodiment of the invention, a portion of the sample is analyzed after having been combined (usually mixed prior to starting the electrophoresis) with the binding partner and another portion of the sample is analyzed using electrophoresis without having been mixed or otherwise combined with the binding partner under otherwise the same conditions. Thereafter a result of the analysis of both portions can be compared to verify whether the analyte of interest is present.

Good results have been achieved with a method according to the disclosure wherein the sample is separated using capillary electrophoresis.

Further, the disclosure teaches a kit for use in the analysis of a sample by capillary electrophoresis, the kit comprising a a) a first container, containing a macromolecule comprising (i) a segment capable of specifically binding to a target compound and a (ii) polyanionic polymer segment; and b) a second container, containing an alkaline buffer for separating the sample by capillary electrophoresis;

c) optionally a capillary for carrying out capillary electrophoresis or a microfluidic device comprising a channel wherein the electrophoresis can be carried out; and d) optionally a container comprising washing fluid for washing the capillary.

The disclosure further teaches a modified antibody or antigen binding fragment thereof, comprising a polyanionic polymer segment, the polyanionic polymer segment having a number average molecular weight of at least 20 kD, in particular of at least 40 kD, more in particular of at least 50 kD.

The disclosure further teaches the use in an electrophoretic analysis of a macromolecule comprising (i) a segment capable of specifically binding to a target compound or group of target compounds which may be present in a sample that is to be analyzed and (ii) a polyanionic polymer segment for selectively modifying the effective mobility of the target compound or group of target compounds which—unbound to the macromolecules—may co-migrate with one or more other compounds of which the presence in the sample is to be determined, whereby the one or more interfering compounds (bound to said macromolecule) migrate into a zone located outside the migration zone of the one or more compounds of which the presence is to be determined.

The disclosure further teaches a kit for use in the analysis of a sample by capillary electrophoresis comprising a first container, containing a macromolecule comprising (i) a segment capable of specifically binding to a target compound and (ii) a polyanionic polymer segment; and a second container, containing an alkaline buffer for separating the sample by electrophoresis. The kit may further comprise a capillary of which the inner wall comprises acidic groups of which at least part dissociate when in contact with the alkaline buffer. The kit may further comprise a third container, containing washing fluid for washing the capillary.

The disclosure further teaches a kit wherein the analysis of a sample is for the diagnosis of a medical disorder, in particular for the diagnosis of a medical disorder selected from the group of gammapathies, paraproteinemias, liver pathologies, alcoholism, renal diseases, including proteinureas, the diagnosis comprising the analysis of an electrophoretic separation of a body fluid sample, said analysis comprising the use of the kit or modified antibody or antigen binding fragment thereof. The analysis of a sample for the diagnosis of a medical disorder would be known to one with skill in the art.

DETAILED DESCRIPTION

Figure 1:
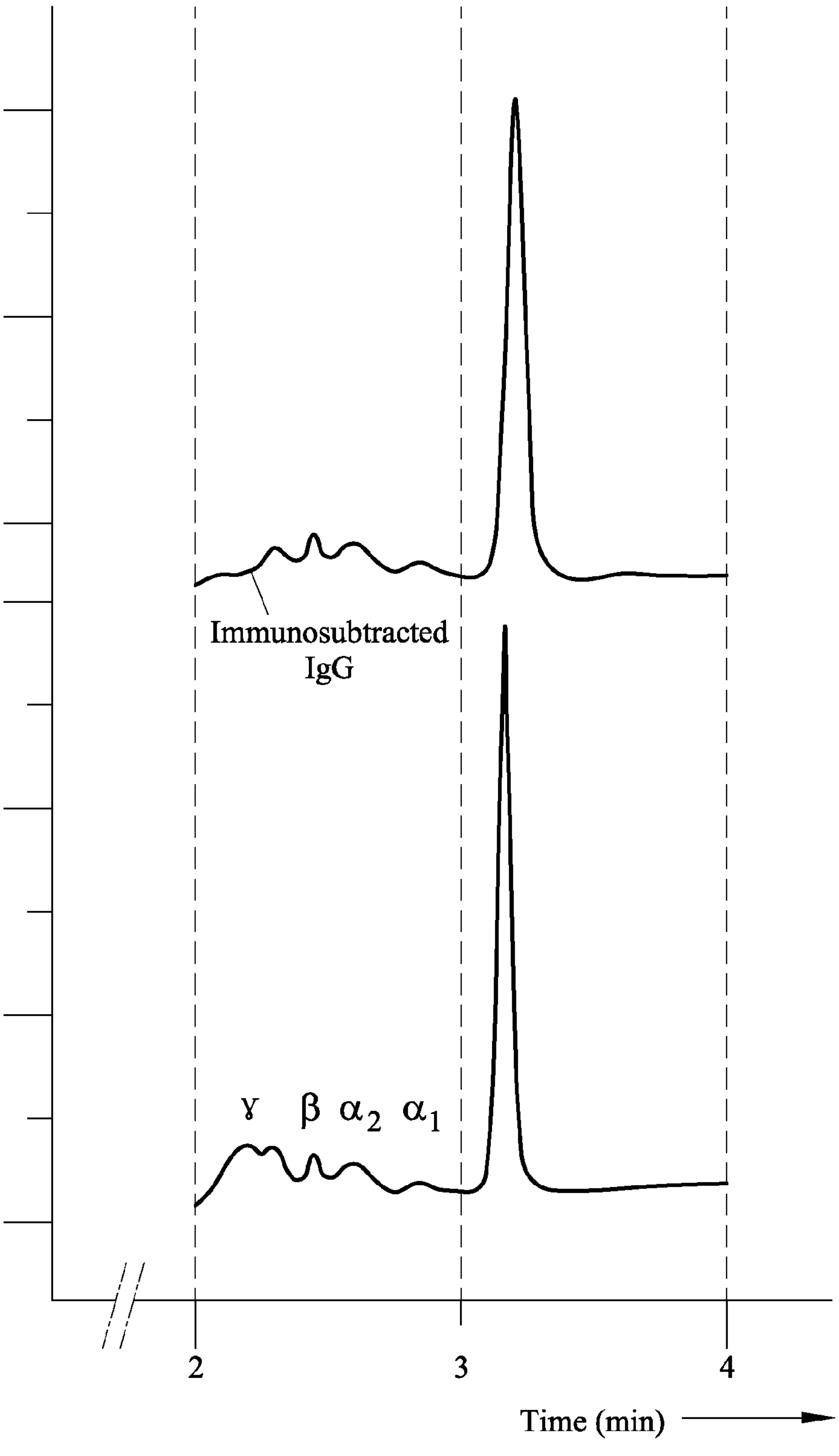
FIG. 1 shows how the proteins bands were separated. The top graph is of the sample to which binding partner (modified antibody) to human immunoglobulins had been added, the bottom graph is of the sample without binding partner.

Unless otherwise indicated, all numbers expressing quantities of ingredients, dimensions reaction conditions and so forth used in the specification and claims are to be understood as being modified in all instances by the term "about".

The term "a" or "an" as used herein means "at least one" unless specified otherwise.

In this application and the claims, the use of the singular includes the plural unless specifically stated otherwise. In addition, use of "or" means "and/or" unless stated otherwise. Moreover, the use of the term "including", as well as other forms, such as "includes" and "included", is not limiting. Also, terms such as "element" or "component" encompass both elements and components comprising one unit and elements and components that comprise more than one unit unless specifically stated otherwise.

Various embodiments of the disclosure could also include permutations of the various elements recited in the claims as if each dependent claim was a multiple dependent claim incorporating the limitations of each of the preceding dependent claims as well as the independent claims. Such permutations are expressly within the scope of this disclosure.

When referring herein to a pH, the pH as measured by a Mettler-Toledo SevenEasy meter with an InLab Expert Pro open junction electrode with integral Argenthal reference electrode and temperature sensor, calibrated by a three-point calibration curve with reference pHs of 4.00, 7.00 and 10.00 at 20° C. is meant, unless specified otherwise.

The disclosure teaches the ability to determine various analytes, particularly, but not exclusively, in complex samples, such as blood serum, urine, cerebrospinal fluid or another body fluid by their selective removal from the electropherogram.

Alternatively, an analysis may be carried out with a reduced level of interference by selectively modifying the migration of a target compound in the sample, which may co-migrate with or otherwise mask the presence of the analyte or analytes of interest.

It is envisaged that a binding partner used in accordance with one embodiment of the invention can be used for modifying the mobility of a variety of target compounds (by complexation or otherwise binding with the target compound), such that both the target compound bound by the binding partner and the unbound binding partner migrate sufficiently remotely from one or more analytes in an electrophoretic separation process to allow baseline separation from said analyte or analytes.

In particular, it has surprisingly been found possible, in accordance with certain embodiments of the invention, to use a binding partner comprising a polyanionic polymer segment which has an electrophoretic mobility (at least at alkaline pH, in particular at a pH above 9) sufficiently different from the mobility of a serum immunoglobulin fraction, preferably also from the beta-fraction of serum proteins, more preferably also from the alpha1-fraction and the alpha2-fraction of serum proteins, in particular also from the albumin fraction and more in particular also from the bis-albumin fraction, to allow base-line separation of said fraction or fractions from both the binding partner unbound to a target compound which may be present in the sample and from the binding partner bound with a target compound (such as an immunoglobulin) that may be present in the sample, at least at an alkaline pH, such as at a pH in the range of 8-11.

Further, it is envisaged that certain embodiments of the invention may allow the use of the binding partner at a relatively low concentration whilst still being effective in changing the migration time of essentially all of the target compound or at least a substantial part thereof in an electrophoretic separation process.

In principle any form of electrophoresis may be used. In particular, good results have been obtained with zone electrophoresis.

In one embodiment, the electrophoresis is carried out in a channel, although in principle a method according to the invention can be carried out on a plate or the like (as in conventional flat gel electrophoresis). In one embodiment, the channel is a capillary, in which case the electrophoresis technique is generally referred to as capillary electrophoresis (CE). In one embodiment, electrophoresis may be carried out in a channel of a microfluidic device or the like, which technique is often referred to in the art as 'CE on a chip'. More information on CE may be found in the review paper 'Clinical Analysis by Microchip Capillary Electrophoresis' by Sam Li and Larry Kricka, *Clinical Chemistry* 52, p 37-45, 2006, and the references cited therein.

The inner wall of the channel (capillary), may in particular comprise acidic groups of which at least a portion dissociate when in contact with the alkaline buffer, such that use can be made of an electro-osmotic flow during the separation. In one embodiment of the invention using capillary electrophoresis, the electro-osmotic flow is directed from the inlet side of the capillary to the outlet side of the capillary, whereby also sample constituents (such as proteins) that have the same sign of charge as the outlet electrode (negative charge) are dragged towards the detector, and thus are detected. Suitable materials are generally known in the art. A much preferred material comprising such acidic groups is silica, in particular fused silica.

The binding partner comprises a segment capable of binding to one or more target compounds (the binding segment) and a polyanionic polymer segment. Typically, the binding partner is a synthetic macromolecule, although the macromolecule may comprise one or more binding segments and/or one or more polyanionic polymer segments that are of biological or synthetic origin. The binding segment may in principle be any natural or synthetic segment capable of specifically binding to a specific target compound (e.g. a specific monoclonal immunoglobulin) or to a specific group of target compounds (e.g. IgG's).

In particular the binding segment can be an antibody or an antigen-binding fragment of the antibody. The antibody or fragment thereof may be commercially available or may be prepared by an immunization technique, which techniques are generally known in the art. An antibody or fragment thereof may in particular be used when the target compound is an antigenic compound, but it is also possible to produce antibodies against compounds that are not antigenic per se, e.g. by immobilizing the compound (which is generally referred to as a hapten) with a macromolecule that is antigenic. Such techniques are also generally known. The binding segment may be a monoclonal or a polyclonal antibody or fragment thereof. Depending on the intended application a polyclonal antibody may be preferred because it may allow modification of the migration of a plurality of closely related target compounds.

On the other hand a monoclonal antibody may be advantageous for targeting a specific target compound with high selectivity. An antibody used as a binding segment may in principle be any type of antibody. For instance it may be a mammalian IgG, IgA, IgE, IgD or IgM, or an other mammalian antibody, for instance an unusual mammalian antibody such as a cammelid single-domain or $V_H$H antibody, or an avian antibody such as IgY.

As is indicated above, it is also possible to use an antigen-binding fragment of an antibody. Such fragments may be produced by enzyme degradation of antibodies, in a manner known in the art per se.

Of these antibodies or fragments thereof, IgG or an antigen-binding fragment thereof is in particular useful as a binding segment. It is considered that IgGs or antigen binding fragments derived from them can be modified particularly well in order to obtain a binding partner suitable for use in the invention.

Other molecules that may be used to provide a binding segment may be selected from the group of protein binding molecules, such as from the group of protein A, avidin, streptavidin, and biotin, receptors (e.g. as found at cell membranes or in the cytoplasm), and other molecules with specific affinity for a binding target of interest.

A polyanionic polymer is a polymer of which at least a substantial part of the monomeric units (from which the polymer is at least conceptually formed) comprises at least one group that is ionisable in an aqueous liquid (of sufficiently high pH), such that the polymer becomes negatively charged. The polymer may be synthetic or natural.

In general, the polyanionic polymer segment comprises a plurality of acid groups having a pKa around or below the pH at which the binding partner is intended to be used, preferably at least 2 pH units below, such that when used in the electrophoretic separation at least the majority of the groups are dissociated (herein the term anionic group may be used for both the non-ionised and the ionised form of an acid group of a polyanionic polymer; likewise when referred to an acid group of a polyanionic polymer this term is meant to include the undissociated acid, the conjugated base and salts thereof). In one embodiment, the polyanionic segment comprises a plurality of acid groups having a pKa of 7 or less. A portion of the monomeric units need not comprise an ionisable group, however it is preferred that 50-100%, in particular 75-100%, more in particular 90-100% of the monomeric groups comprise one or more groups that are ionisable to form an anionic group at alkaline pH.

Examples of ionised groups of a polyanionic polymer segment in particular include, but are not limited to, carboxylate functions, sulphate functions, sulphonate functions, phosphate functions and phosphonate functions.

In one embodiment, the polyanionic polymer segment is selected from the group of polyanionic poly(amino acids), poly(carboxylic acids), poly(sulphonic acids), polynucleotides, carboxylated polysaccharides, sulphated polysaccharides and phosphorylated polysaccharides, including copolymers thereof.

In one embodiment, the polyanionic polymer segment is a poly(amino acid). The poly(amino acid) usually has a plurality of acid side-groups. These side-groups may be a side-group of a natural amino acid having a carboxylic acid side-group, such as glutamic acid or aspartic acid, or another acidic group, such as a hydroxyl function (as in tyrosine, having a pKa of about 10). In one embodiment of the invention, the polyanionic polymer segment is a poly(amino acid) segment, of which a plurality of amine side-groups (e.g. a plurality of lysine amino acid residues) have been derivatised to form an acid group. To achieve this, such functions may be reacted with a polyacid or anhydride thereof, e.g. dicarboxylic acid, a tricarboxylic acid or a carboxylic acid having more than three carboxylic acid functions. In particular, the amine side group may have been derivatised with succinic acid, mellitic acid, benzene tricarboxylic acid, a sulphonic acid a phosphoric acid, or an anhydride of any of these. Such poly(amino acids) may be purchased commercially or derivatised in a manner known per se, e.g. in the prior art mentioned above.

In one embodiment, the poly(amino acid) segment is a poly(amino acid) segment comprising a plurality of lysine residues of which at least the majority of the amine-side-groups have been transformed into anionic side groups, preferably by carboxylation, e.g. by succinylation, in particular polylysine wherein 90-100%, or preferentially 98-100% of the amine side groups have been transformed into anionic side groups. A binding partner comprising such a segment has been found particularly advantageous for use in a method wherein a sample is analysed for the presence of a serum protein.

In one embodiment a polyanionic segment comprising polyaspartic acid or polyglutamic acid is provided.

In one embodiment the anionic segment comprises a polyarginine, polyasparagine, polyglutamine or polyhistidine segment of which at least the majority of the amine-side-groups (preferably 90-100%) have been transformed into anionic side groups, preferably by reaction with succinic acid or another polycarboxylic acid or anhydride thereof.

An anionic polysaccharide segment may be selected from the group of carboxyalkyl celluloses, such as carboxymethyl celluloses; heparins; sulphated dextrans; hyaluronic acids and the like.

A suitable polysulphonic acid is poly(4-styrenesulphonic acid).

Suitable polycarboxylic acids may be selected from the group consisting of polymaleic acids, polyacrylic acids, polymethacrylic acids and polyfumaric acids, including copolymers thereof. A suitable copolymer is, for instance, a poly(4-styrenesulphonic acid-co-maleic acid) copolymer.

The average size (molecular weight) of the polymer may be chosen within wide limits, in particular depending on its intended use. It has been found that the effective mobility of a complex of a target compound and the binding partner may increase (i.e. becomes more negative) with increasing polyanionic polymer segment molecular mass (at a similar mass over charge ratio of the segment). Thus, it is contemplated that by choosing the average molecular weight of the polyanionic polymer segment the desired mobility of the target compound-binding partner complex may be fine-tuned.

As used herein the (average) molecular weight is the (average) molecular weight based on matrix assisted light scattering spectrometry (MALLS) or on viscosity (as specified by the supplier if a commercially obtained polymer is used to prepare the binding partner), or the (average) molecular weight as determined by analytical ultracentrifugation (AUC).

The number average molecular weight (which is determinable by AUC) of the polyanionic polymer segment may be at least 1 kg/mol, at least 10 kg/mol or at least 20 kg/mol. In certain embodiments, the number average molecular weight is at least 40 kg/mol, more preferably at least 50 kg/mol or at least 75 kg/mol.

The upper-limit is primarily defined by solubility/dispersibility of the binding partner. Further, the larger the polymeric segment, the higher the viscosity tends to be. Thus, usually the polymeric segment chosen has an average molecular weight such that the viscosity of the sample comprising the binding partner is still easy to handle. The skilled person will know how to determine a suitable upper viscosity and molecular weight. In general the number average molecular weight will by 10000 kg/mol or less, preferably 5000 kg/mol or less, in particular 1000 kg/mol or less, more in particular 750 kg/mol or less.

The sample preferably is a biological sample, in particular a sample comprising a body fluid, more in particular a sample comprising a body fluid selected from blood plasma, blood serum, lymph fluid, urine or cerebrospinal fluid.

The analyte may be any analyte that can be separated by electrophoresis (including any analyte separable by electrokinetic chromatography). The analyte may be selected from biomolecules, and may comprise proteins and other peptides. The analyte may be the target compound or a compound that is likely to co-migrate with the target compound in the absence of the binding partner. The analyte may be a marker for a disorder, such as a disorder selected from gammapathies, paraproteinemias, liver pathologies and alcoholism.

Examples of analytes are serum proteins, in particular a serum protein selected from the group of immunoglobulins; transferrins; albumin; bis-albumin; microglobulins, such as beta-2 microglobulin; and macroglobulins, which may be an immunoglobulin, such as IgM, or may be another macroglobulin, such as alpha-2 macroglobulin.

The separation conditions may be based on a method known per se, e.g. in the above described prior art for the analysis of a specific analyte. Also buffer solutions for electrophoresis are commercially available, for various analytes.

In general it is advantageous to use a buffer solution having a pH that is about the same as or higher than the (average) pKa of the polyanionic polymer segment, such that at least the majority of the acid functions are ionized to form anionic groups. In particular, the separating of the sample may be carried out using a solution having an alkaline pH, in particular a pH in the range of pH 8.0 to 11.0, more in particular a pH in the range of pH 9.0 to 10.7, even more in particular in the range of 9.5-10.5. In one embodiment, the solution comprises a pH-buffer. Such buffer is in general a combination of at least one acid and at least one base (which may be the conjugated base of the acid), with a pKa of about the pH of the solution (generally the pKa being in the range of pH +/−1 pH unit, preferably in the range of +/−0.5 pH units).

Examples of acid/bases that may be used to provide buffer solutions include, but are not limited to, borate, phosphate and carbonate buffers, buffers based on amino acids and zwitterionic compounds for providing buffers, known as biological buffers. Examples of acids/bases for biological buffers include bis-TRIS (2-bis[2-hydroxyethyl]amino-2-hydroxymethyl-1,3-propanediol), ADA (N-[2-acetamido]-2-iminodiacetic acid), ACES (2-[2-acetamino[-2-aminoethanesulphonic acid), PIPES (1,4-piperazinediethanesulphonic acid), MOPSO (3-[N-morpholino]-2-hydroxypropanesulphonic acid), bis-TRIS PROPANE (1,3-bis[tris(hydroxymethyl)methylaminopropane]), BES (N,N-bis[2-hydroxyethyl]-2-aminoethanesulphonic acid), MOPS (3-[N-motpholino]propancsulphonic acid), TES (2-[2-hydroxy-1,1-bis(hydroxymethyl)ethylamino]ethanesulphonic acid), HEPES (N-[2-hydroxyethyl] piperazine-N'-(2-ethanesulphonic)acid), DIPSO (3-N,N-bis [2-hydroxyethyl]amino-2-hydroxypropanesulphonic acid), MOBS (4-N-morpholinobutanesulphouic acid), TAPSO (3-[N-tris-hydroxymethyl-methylamino]-2-hydroxypropane-sulphonic acid), TRIS (2-amino-2-[hydroxymethyl]-1,3-propanediol), HEPPSO(N-[2-hydroxyethyl]piperazine-N'-[2-hydroxypropanesulphonic]acid), POPSO (piperazie-N,N'-bis[2-hydroxypropanesulphonic]acid), TEA (triethanolamine), EPPS(N-[2-hydroxyethyl]-piperazine-N'-[3-propanesulphonic]acid), TRICINE (N-tris[hydroxymethyl]methylglycine), GLY-GLY (diglycine), BICINE (N,N-bis[2-hydroxyethyl]glycine), HEPBS (N-[2-hydroxyethyl] piperazine-N'-[4-butanesulphonic]acid), TAPS(N-tris [hydroxymethyl]methyl-3-aminopropanesulphonic acid), AMPD (2-amino-2-methyl-1,3-propanediol), TABS (N-tris [hydroxymethyl]methyl-4-aminobutanesulphonic acid), AMPSO (3-[(1,1-dimethyl-2-hydroxyethyl)amino]-2-hydroxypropanesulphonic acid), CHES (2-(N-cyclohexylamino)ethanesulphonic acid), CAPSO (3-[cyclohexylamino]-2-hydroxy-1-propanesulphonic acid), AMP (2-amino-2-methyl-1-propanol), CAPS (3-cyclohexylamino-1-propanesulphonic acid) and CABS (4-[cyclohexylamino]-1-butanesulphonic acid).

Analysis of serum proteins use may be made of a buffer solution having a pH in the range of pH 9.0 to 10.7. Suitable kits comprising a buffer and instructions are commercially available, e.g. CE-Sure SPE kit, available since the mid 1990's, from Helena Biosciences (Gateshead, UK). Furthermore, in US 2002/0162744, which describes an additive that interacts with at least one serum protein, in particular albumin, and modifies its electrophoretic mobility, an alkaline buffer solution of pH 10 is described. Similarly, the separation of serum transferrin sialoforms may for instance be carried out at a pH in the range of 8-9, in a buffer solution comprising borate and diaminobutane, e.g. as described in Journal of Chromatography B, 742 (2000), 79-89.

Various embodiments of the invention will now be illustrated by the following examples.

EXAMPLES

The following examples are provided for illustrative purposes only and are not intended to limit the scope of the invention.

Example 1

Immunodisplacement CE Using an Antibody Modified with a Poly(Amino Acid)

Preparation of Binding Partner

The modified antibody was thereafter Fluid A: antibody (Sheep anti-human IgG kappa, 8 mg/ml) was dialysed overnight into 100 mM Sodium Phosphate, 900 mM NaCl pH 7.4. 500 μl of this antibody solution were used per reaction.

Fluid B: 10 mg poly(amino acid) was dissolved in 250 ml 100 mM Sodium Phosphate, 900 mM NaCl, pH 7.4.

Fluid C: 10 mg NHS(N-hydroxysulphosuccinimide sodium salt) was dissolved in 40 μl 100 mM Sodium Phosphate, 100 mM NaCl, pH 7.4.

Fluid D: 10 mg EDC(N-(3-dimethylaminopropyl)-N'-ethylcarbodiimide hydrochloride) dissolved in 40 μl 100 mM Sodium Phosphate, 100 mM NaCl, pH 7.4.

Fluids A, B, C and D were combined and mixed to form a reaction mixture by vortexing. The reagents in the mixture were allowed to react overnight at room temperature (about 20° C.) whilst being mixed end-over-end on a rotator, thereby forming an antibody to which poly(amino acid) is covalently linked, i.e. the modified antibody or binding partner.

Thereafter the reaction mixture was dialysed against a 50 mM Sodium Phosphate solution, 200 mM NaCl, pH 8.1, using 100 kg/mol molecular weight cut-off dialysis concentrated by placing the dialysis tubing containing the modified antibody in Spectra/Gel absorbent (Spectrum Labs, Rancho Dominguez, Calif., USA.)

After the concentration step, a solution of 50 mM Sodium Phosphate, 200 mM NaCl, pH 8.1 was added to the antibody solution, up to a volume of 5004

Sample Preparation for Immunodisplacement CE

2 μl of human blood serum was added to 98 μl of CE buffer solution The buffer was 200 mM CAPS, 66 mM TAPS in water, pH 9.7, and mixed. Thereafter 20 μl modified antibody solution was added. After mixing, the sample was ready for separation by CE.

Immodisplacement Electrophoresis

The CE system configuration was as follows:

Instrument: PrinCE CEC 760, DAx 3D 8.1 software
Capillary: fused silica (no internal coating)
Capillary length to detector: 23 cm
Total capillary length: 30 cm
Capillary internal diameter: 50 μm Sample was injected using pressure injection (25 mbar, 6 sec) and for the separation 13 kV was applied. The temperature was 25° C.

Further, a serum sample was prepared and separated in the same way, with the exception of adding the modified antibody.

Example 1A

Polylysine succinylate Modified Antibody

Sheep anti-human IgG was modified with poly-L-Lysine succinate (Sigma-Aldrich, catalogue nr. P3513, Mw>50 000 g/mol, Mw based on poly-L-lysine viscosity, also assed by MALLS) as described above.

The serum sample was a human serum normal control sample, i.e. a sample from a healthy human.

FIG. 1 shows how the proteins bands were separated. The top graph is of the sample to which binding partner (modified antibody) to human immunoglobulins had been added, the bottom graph is of the sample without binding partner. As is shown in FIG. 1, the binding partner was effective in binding to immunoglobulins in the serum and neither the binding partner itself nor the complex of binding partner with human immunoglobulins migrated within or near the serum protein bands. The separation was stopped after 4 min (about 45 sec after the last band (albumin) had fully migrated past the detector), at which time neither the complex nor uncomplexed binding partner had yet migrated past the detector. This illustrates that a binding partner according to the present invention is particularly suitable for use in the analysis of serum proteins.

Example 1B

Poly-L-glutamic Acid Modified Antibody

Sheep anti-human IgG was modified with poly-L-glutamic acid (Sigma-Aldrich catalogue number P4886, molecular weight 50000-100000 g/mol, 64000 g/mol average, determination based on viscosity and by MALLS) as described above.

Thereafter a human blood serum sample with an abnormal gamma-band level (a so-called abnormal control sample) to which poly-L-glutamic acid modified antibody had been added (as above) and a sample to which no modified antibody had been added where separated with CE (as above). It was found that the modified antibody was effective in almost completely removing the abnormal human immunoglobulin in the gamma band. The last serum protein band (albumin) fully migrated within 3 min 15 sec. After 4 min the separation was stopped, at which time no modified antibody or complex thereof with human immunoglobulin had been detected yet.

Example 1C

Poly-gamma Gutamic Acid Modified Antibody

Sheep anti-human IgG was modified with poly-gamma-glutamic acid (PGGA) (Natto Biosciences, Montreal, Canada), with molecular weights of 390 kg/mol or 2250 kg/mol as described above using 5 mg poly(amino acid) per modification reaction.

Figure 2:
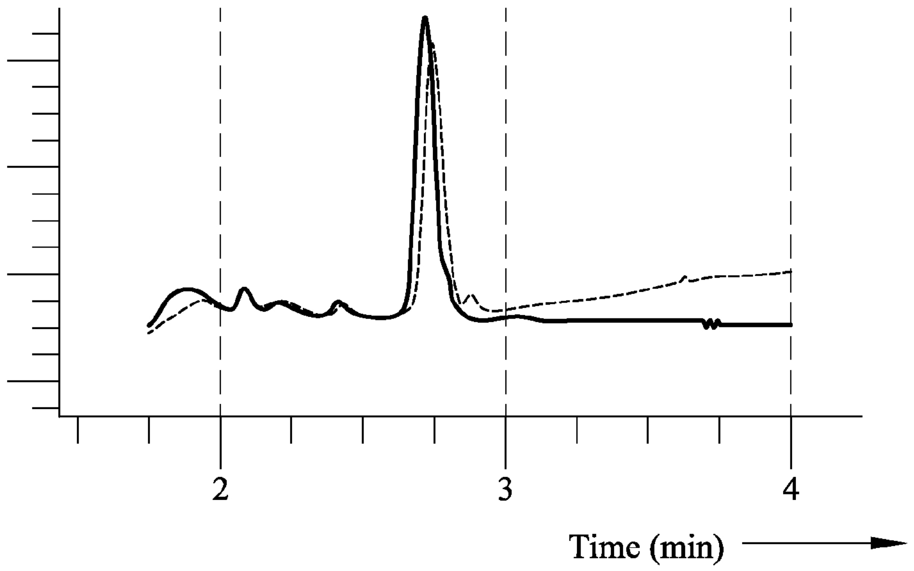
FIG. 2 shows results of modified antibodies added to a serum control sample; 390 kg/mol. The dashed lines represent the samples treated with the modified antibody, the solid lines the samples without added modified antibody
Figure 3:
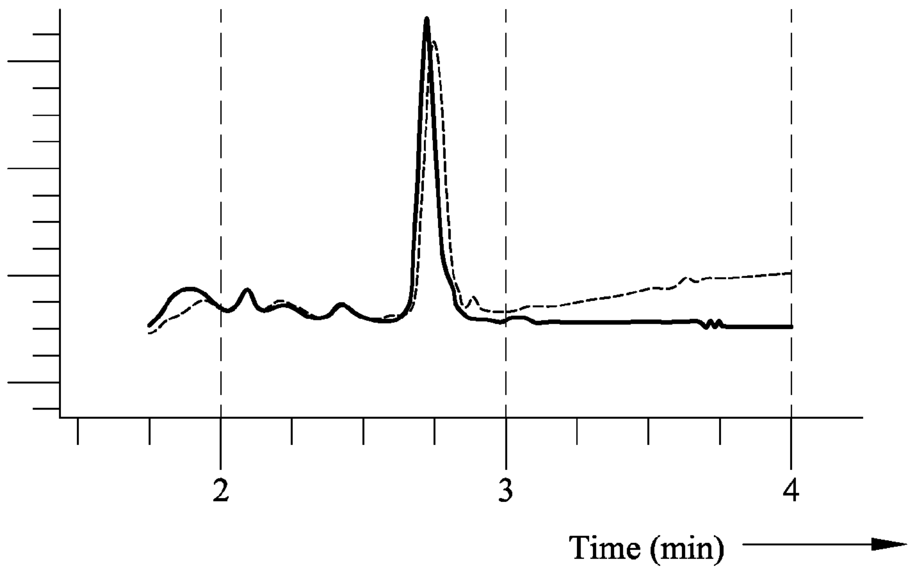
FIG. 3 shows results of modified antibodies added to a serum control sample 2250 kg/mol. The dashed lines represent the samples treated with the modified antibody, the solid lines the samples without added modified antibody.

Each of the modified antibodies were added to a serum control sample, as described above. The results are shown in FIG. 2 (390 kg/mol) and 3 (2250 kg/mol). The dashed lines represent the samples treated with the modified antibody, the solid lines the samples without added modified antibody. It can be seen that in each of the tests the modified antibody is effective in removing human immunoglobulin from the gamma band and that the immunodisplaced human immunoglobulin as well as the modified antibody migrate after the last serum protein band (albumin).

Example 2

Immunodisplacement CE Using an Antibody Modified with a Carboxylated Polysaccharide Preparation of Binding Partner The same protocol was used as described in Example 1, with the proviso that the amounts of polyanionic polymer, in this case two different carboxymethyl celluloses (CMC), were varied as follows:

Of a CMC sodium salt, average Mw 90 000 g/mol (Aldrich product number 419273) 2, 5 or 10 mg were used to modify the sheep anti-human IgG.

Of a CMC sodium salt average Mw 250 000 g/mol (Aldrich product number 419303) 2, 4 or 6 mg were used.

Sample Preparation for Immunodisplacement CE

Human abnormal control serum samples were prepared as described above, with or without binding partner.

Immodisplacement Electrophoresis

CE separations were carried out as described above. It was found that binding partners modified with either type of CMC were effective in binding to immunoglobulins in the serum samples and causing the immunoglobulins bound to the binding partners to migrate after the last serum protein band (albumin). It was found that the binding partner comprising CMC having an average molecular weight of 90 000 g/mol (complexed with human immunoglobulin) migrated closer to the last serum protein band than the binding partner comprising CMC having an average molecular weight of 250 000 g/mol (complexed with human immunoglobulin), although for both types of binding partners a baseline separation between the binding partner (complex) and albumin was feasible.

It was further found that the resolution between binding partner (complex) and albumin was higher when for the binding partner obtained by adding 4, 5, 6 or 10 mg CMC than for the binding partner obtained by adding only 2 mg CMC.

Example 3

Immunodisplacement CE Using an Antibody Modified with a Sulphonic Acid Carboxylic Acid Copolymer Preparation of Binding Partner Two poly(4-styrenesulphonic acid-co-maleic acid) polymers (PSSA-MA) were used to modify anti-human antibody. The PSSA-MAs, obtained from Sigma-Aldrich, both had an average molecular weight of about 20 000 g/mol. One PSSA-MA had a styrene sulphonic acid to maleic acid molar ratio of 1:1 (Aldrich catalogue number 434558), the other had a styrene sulphonic acid to maleic acid molar ratio of 3:1 (Aldrich catalogue number 434566)

The same protocol was used as described in Example 1, with the proviso that the amounts were 15 mg or 20 mg, instead of 10 mg.

Sample Preparation for Immunodisplacement CE

Human abnormal control serum samples were prepared as described above, with or without binding partner.

Immodisplacement Electrophoresis

CE separations were carried out as described above.

It was found that the binding partners modified with either type of PSSA-MA were effective in binding to immunoglobulins in the serum samples and causing the immunoglobulins bound to the binding partners to migrate after the last serum protein band (albumin).

The description of the present invention has been presented for purposes of illustration and description, but is not intended to be exhaustive or limiting of the invention to the form disclosed. The scope of the present invention is limited only by the scope of the following claims. Many modifications and variations will be apparent to those of ordinary skill in the art. The embodiments described and shown in the figures were chosen and described in order to best explain the principles of the invention, the practical application, and to enable others of ordinary skill in the art to understand the invention for various embodiments with various modifications as are suited to the particular use contemplated.

While the invention has been particularly shown and described with reference to a number of embodiments, it would be understood by those skilled in the art that changes in the form and details may be made to the various embodiments disclosed herein without departing from the spirit and scope of the invention and that the various embodiments disclosed herein are not intended to act as limitations on the scope of the claims. All references cited herein are incorporated in their entirety by reference.

What is claimed is:

1. A method for the analysis of a sample comprising one or more proteins, wherein the sample is selected from the group consisting of blood serum and urine, the method comprising the steps of:

a. separating a first portion of the sample by electrophoresis into constituent parts;

b. mixing a second portion of the sample with a binding partner for a target compound or a group of target compounds, wherein the target compound or the group of the target compounds comprise an immunoglobulin, and the binding partner is a macromolecule comprising:

(i) a binding segment capable of specifically binding to the target compound or the group of the target compounds, the binding segment selected from the group consisting of antibodies and fragments thereof; and (ii) a polyanionic poly(amino acid);

wherein the binding segment and the polyanionic poly (amino acid) are covalently linked;

wherein the mixing of the binding partner and the target compound or the group of the target compounds produces a complex; and c. separating the second portion by electrophoresis into constituent parts, wherein a protein or proteins of the sample that have not produced a complex with the binding partner are separated from the complex of the binding partner with the target compound or the group of the target compounds in a separation medium in which the binding partner has a net negative charge and wherein a non-complexed binding partner and the complex of the binding partner with the target compound or the group of the target compounds are migrated out of protein bands;

d. comparing the separated constituent parts of step (a) with the separated constituent parts of step (c).

2. The method according to claim 1, wherein the polyanionic poly(amino acid) is selected from the group consisting of polylysines of which 90-100% of the amine-side-groups have been transformed into anionic side groups, polyarginines of which 90-100% of the amine-side-groups have been transformed into anionic side groups, polyhistidines of which 90-100% of the amine-side-groups have been transformed into anionic side groups, polyasparagines, of which 90-100% of the amine-side-groups have been transformed into anionic side groups, polyglutamines of which 90-100% of the amine-side-groups have been transformed into anionic side groups, polyglutamic acids and polyaspartic acids.

3. The method according to claim 2, wherein the polyanionic poly(amino acid) is selected from the group of polylysines of which 90-100% of the amine-side-groups have been modified with a polycarboxylic acid or anhydride thereof.

4. The method of claim 2, wherein the polyanionic poly (amino acid) comprises polylysines having 90-100% of the amino-side chain-groups transformed into anionic side groups.

5. The method according to claim 1, wherein the polyanionic poly(amino acid) has a number average molecular weight of at least 20 kD.

6. The method according to claim 1, wherein the separating of the sample is carried out using a buffer having a pH in the range of pH 8.0 to 11.0.

7. The method according to claim 1, wherein the analysis comprises qualitatively determining the presence of the target compound or the group of the target compounds.

8. The method of claim 7, wherein the target compound or the group of the target compounds comprises IgG.

9. The method of claim 7, wherein the target compound or the group of the target compounds comprises IgM.

10. The method of claim 7, wherein the group of the target compounds comprises both IgG and IgM.

11. The method according to claim 1, wherein the analysis comprises quantitatively determining the presence of the target compound or the group of the target compounds.

12. The method of claim 11, wherein the target compound or the group of the target compounds comprises IgG.

13. The method of claim 11, wherein the target compound or the group of the target compounds comprises IgM.

14. The method of claim 11, wherein the group of the target compounds comprises both IgG and IgM.

15. The method of claim 1, wherein the sample is a blood serum sample.

16. The method of claim 1, wherein the sample is a urine sample.

17. The method according to claim 1, wherein the electrophoresis is carried out in a channel.

18. The method according to claim 17, wherein said electrophoresis carried out in a channel is capillary electrophoresis.

19. The method of claim 1, wherein the electrophoresis is capillary zone electrophoresis.

* * * * *